(12) United States Patent
Johnson et al.

(10) Patent No.: US 7,004,040 B2
(45) Date of Patent: Feb. 28, 2006

(54) SUPPORT STRUCTURE FOR A LOAD-BEARING DEVICE

(75) Inventors: Thomas H. Johnson, Winnebago, MN (US); Robert J. Hall, Fairmont, MN (US)

(73) Assignee: Avery Weigh-Tronix, LLC, Fairmount, MN (US)

( * ) Notice: Subject to any disclaimer, the term of this patent is extended or adjusted under 35 U.S.C. 154(b) by 0 days.

(21) Appl. No.: 10/741,476

(22) Filed: Dec. 18, 2003

(65) Prior Publication Data

US 2005/0132819 A1    Jun. 23, 2005

(51) Int. Cl.
*G01L 1/04* (2006.01)
(52) U.S. Cl. ................................. 73/862.636
(58) Field of Classification Search .......... 73/862.629, 73/862.631, 862.632, 862.636, 862.637, 73/862.638
See application file for complete search history.

(56) References Cited

U.S. PATENT DOCUMENTS

| | | | | |
|---|---|---|---|---|
| 4,804,053 A | * | 2/1989 | Nordstrom | ................ 177/211 |
| 4,843,888 A | * | 7/1989 | Gram et al. | ................... 73/856 |
| 5,347,387 A | * | 9/1994 | Rice | ............................ 398/129 |
| 5,515,829 A | * | 5/1996 | Wear et al. | ................. 123/446 |
| 5,538,364 A | * | 7/1996 | Huntsman | ................... 405/288 |
| 6,005,199 A | * | 12/1999 | Harada et al. | .............. 177/211 |

\* cited by examiner

*Primary Examiner*—Max Noori
(74) *Attorney, Agent, or Firm*—DLA Piper Rudnick Gray Cary US LLP

(57) ABSTRACT

A mechanism for reducing horizontal force in load measurement is presented. The mechanism includes a structure having surfaces of nonuniform radii of curvature (e.g., oblate spheroid surfaces) at both ends. The ends of the structure contact a force-sensor coupling element and a base-coupling element, forming two interfaces. Each interface includes a contact area between a convex surface and a concave surface. When a horizontal force is applied, the contact area at each interface shifts, allowing the structure to tip from the vertically aligned position that it is in when no horizontal force is applied. Compared to conventional mechanisms, the structure of the invention has a lower effective height because interfaces between oblate spheroid surfaces allow a larger angle of deflection than flat interfaces. The oblate spheroid interfaces also allow deflection to occur with less wear and tear at the interfaces compared to the flat-interfaced structures.

16 Claims, 9 Drawing Sheets

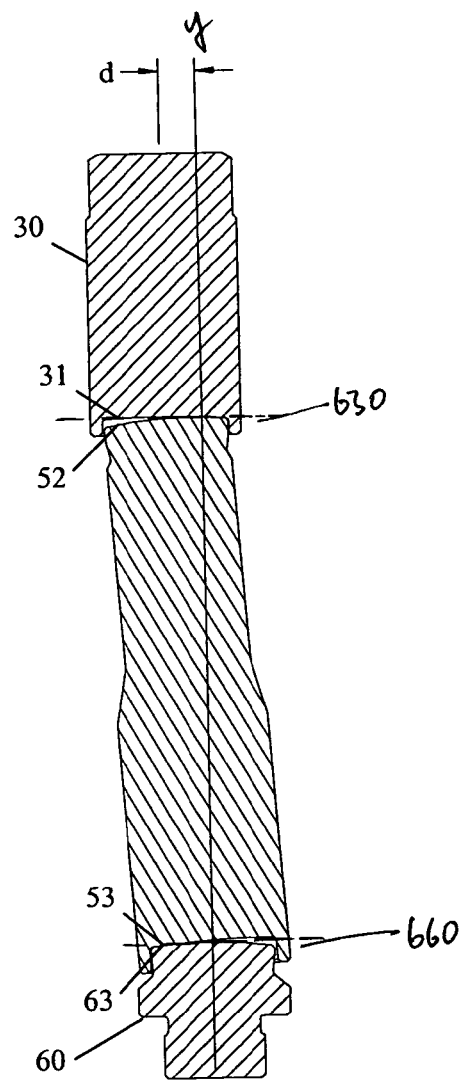
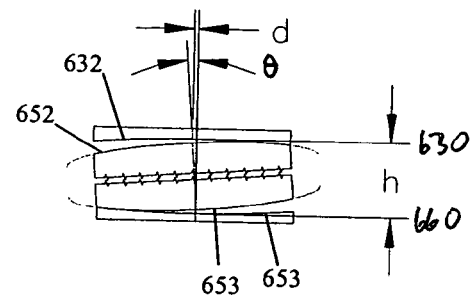
FIG. 6B
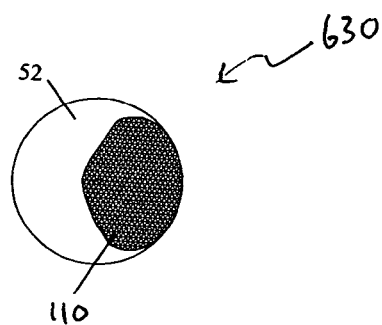
FIG. 6C
FIG. 6A

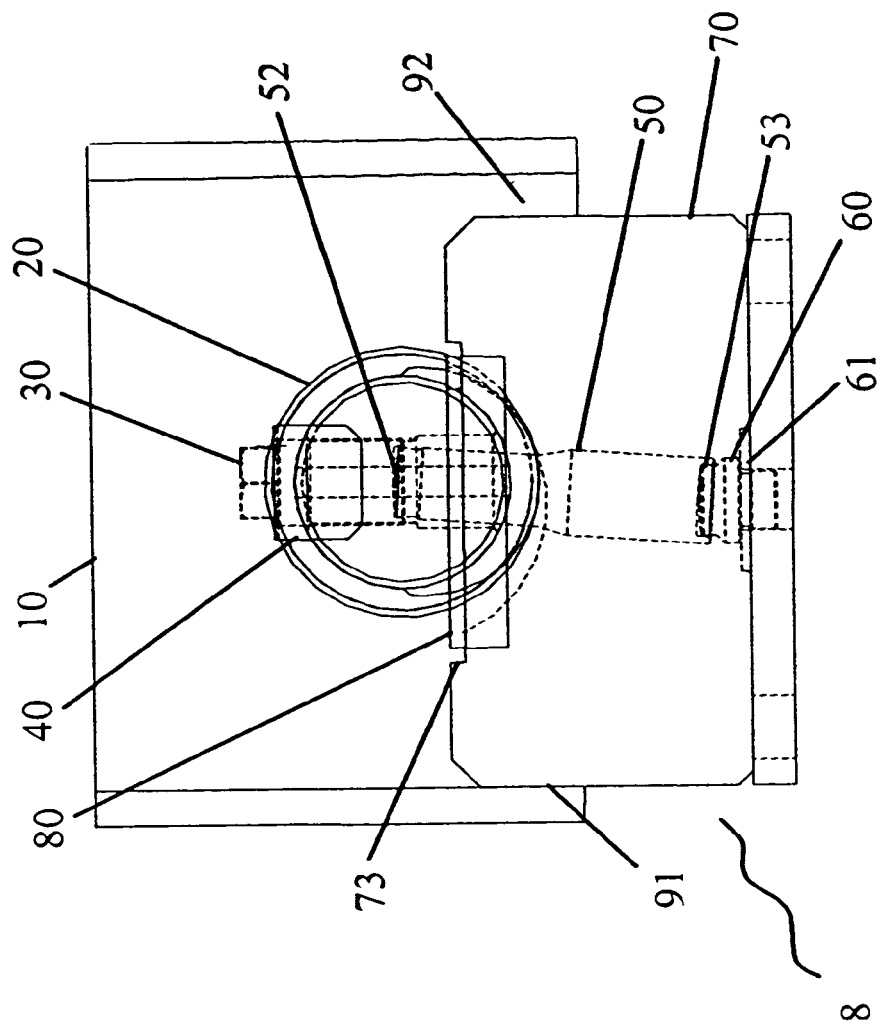
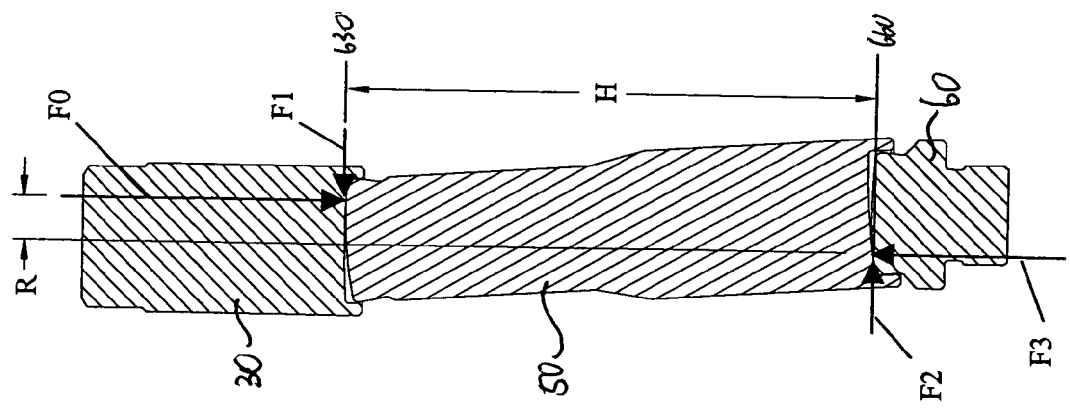
Fig. 8
Fig. 7

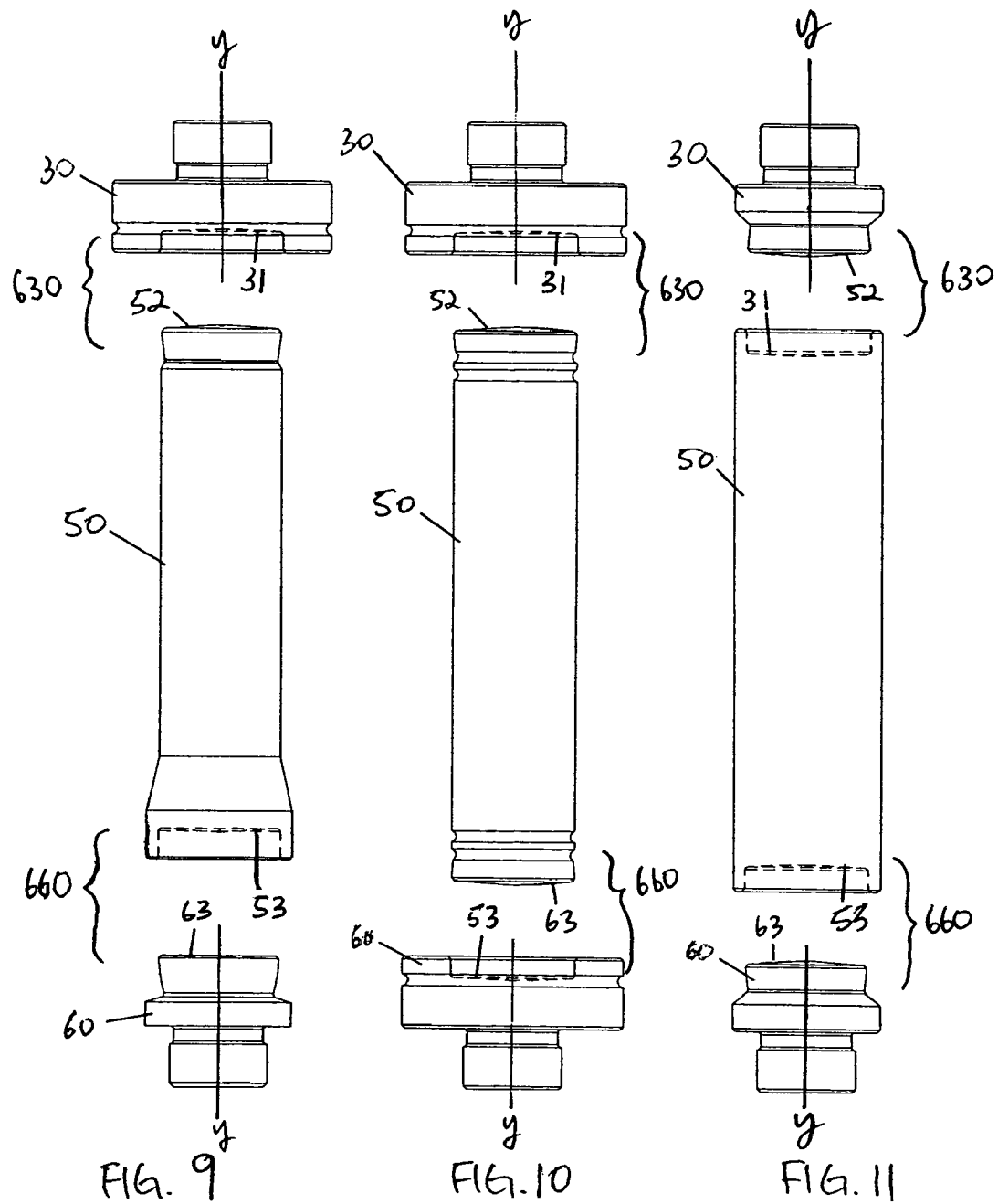

SUPPORT STRUCTURE FOR A LOAD-BEARING DEVICE

FIELD OF THE INVENTION

The invention relates generally to a load-bearing device for force transfer and particularly to a scale support element for improved measurement of force.

BACKGROUND OF THE INVENTION

Various load measuring devices and scales are known in the art. For example, U.S. Pat. No. 3,650,340 to Richard S. Bradley discloses a bending-beam structured load cell that is resistant to torque, moment, and end-forces, all of which affect the accuracy of the load cell. Most of the currently available scales generally depend on the stability of the loaded structure between the load cells for output stability and reduction of horizontal forces. For example, scales made by Weigh-Tronix utilizing multiple load cells provide chain links to reduce horizontal forces between load cells and absorb the energy from horizontal movement of the load on the scale. Other scales provide vertical cables to reduce diverse forces such as horizontal forces, thereby providing a substantially collimated force in the direction of force measurement. "Diverse forces" are herein used to refer to forces that are not in the direction of force measurement, while "collimated forces" are in the direction of force measurement. In the context of weight measurement, a vertical force would be a collimated force and horizontal forces would be diverse forces.

These scales, while reducing the adverse effect on measurement accuracy that is caused by horizontal forces, are expensive. The high cost associated with these scales are at least partly due to the massive support structures that are needed to suspend the flexible tension elements located between the load bearing structures and the load cells to reduce diverse forces horizontal forces between the load cells.

Although scales exist that do not require these massive and expensive support structures, these scales have other problems. Some scales include flexible compressive elements between the load cells and the load bearing structures. For example, scales made by Mettler Toledo and Cardinal provide rocker pins that are load cells with spherical ends and spherical or flat cups to reduce the horizontal forces. However, these scales are problematic in that they do not dampen the vibration or absorb energy adequately to prevent undesirable effects to the scale and on the force measurement when the scale is disturbed by the load. Although they can be made to dampen vibration and absorb adequate energy, doing so requires equipping these scales with an expensive check-rod system.

Some load cell manufacturers thread leveling feet into load cells with rubber pads to reduce the horizontal forces between the load cells that are coupled through the floor of the scale. These load cells must have large pads to support heavy loads because of the low load bearing strength of rubber pads. Rubber pads require level surfaces, vertically aligned feet, and rigid support structures. Otherwise, twisting and bending of the load cells due to diverse forces create errors in the load cell outputs.

Some other load cells get around this strict requirement for level surfaces by using leveling feet that are connected to the load cells with pivot joints. This arrangement allows uneven floors and misalignment but only reduces the forces caused by bending of the support structure.

What is needed is a durable load-transfer device that rapidly stabilizes and isolates r collimates vertical force in a cost-effective manner.

SUMMARY OF THE INVENTION

A support mechanism for reducing the horizontal force components on load measurement is presented. The support mechanism includes a structure having two ends with non-uniform radii of curvature separated by a distance. The two ends may include oblate spheroid surfaces. The ends of the structure contact a force-sensor coupling element and a base-coupling element, forming two interfaces. Each interface includes a contact area between a convex surface and a concave surface. When a horizontal force is applied, the contact area at each interface shifts, causing the structure to tip from the vertically aligned position that it is in when no horizontal force is applied. Compared to conventional support mechanisms, the support mechanism of the invention has a lower effective height because the interfaces between oblate spheroid surfaces allow a larger angle of deflection than spherical or flat interfaces while still limiting contact stress levels. Also, the surfaces with non-uniform radii of curvature interfaces allow deflection to occur with less wear and tear at the interfaces compared to the spherical- and flat-interfaced support structures. The support mechanism may be used, for example, in a load cell.

In another aspect, the invention is a method of reducing the effect of diverse forces or horizontal force on load measurement by using interfaces of two oblate spheroidal surfaces or surfaces with non-constant curvature. More specifically, the method includes coupling a structure to a first force coupling mechanism by placing a first surface with non-constant curvature in contact with a first counterpart surface with non-constant curvature to form a first contact surface. Similarly, a second contact surface is formed by coupling the structure to a second force coupling mechanism. This coupling is done by placing a second surface of the structure in contact with a second counterpart surface, wherein both the second surface and the second counterpart surface have a non-constant curvature. The first and second contact surfaces shift positions when the structure tips from a vertically aligned position in response to horizontal force. The structure returns to its original vertically aligned position upon removal of the horizontal force with minimal oscillation.

BRIEF DESCRIPTION OF THE DRAWINGS

FIG. 6A is a cross-sectional view of the support structure of FIG. 4B, in a deflected state;

FIG. 6B is a cross-sectional view of the interfaces in a support structure in accordance with the invention, in a deflected state;

FIG. 6C is an illustration of an interface of the support structure at an interface, in a deflected state;

FIG. 7 is an illustration of the forces on the support structure of FIG. 6A;

FIG. 8 is an end view of the load-measuring device of FIG. 2A, wherein the support structure is in a deflected state;

FIGS. 9, 10, and 11 depict different embodiments of the support structure in accordance with the invention;

DETAILED DESCRIPTION OF THE PREFERRED EMBODIMENT

Embodiments of the invention are described herein in the context of a load cell and more specifically in the context of a multi-load-cell scale. However, it is to be understood that the embodiments provided herein are just preferred embodiments, and the scope of the invention is not limited to the applications or the embodiments disclosed herein. For example, the supporting structure may be used in any application where it is desirable to reduce diverse forces that act in a direction other than the direction of interest. Also, although cylindrical embodiments of the support structure are disclosed, the support structure may have any shape that suits a particular application. Although oblate spheroid surfaces are disclosed, a person of ordinary skill in the art will understand that any suitable rotated surface with a non-constant curvature, such as parabolic, hyperbolic, sinusoidal, and exponential surfaces, may function as the invention depending on the application and deformation of the interfaces under the load.

Figure 1:
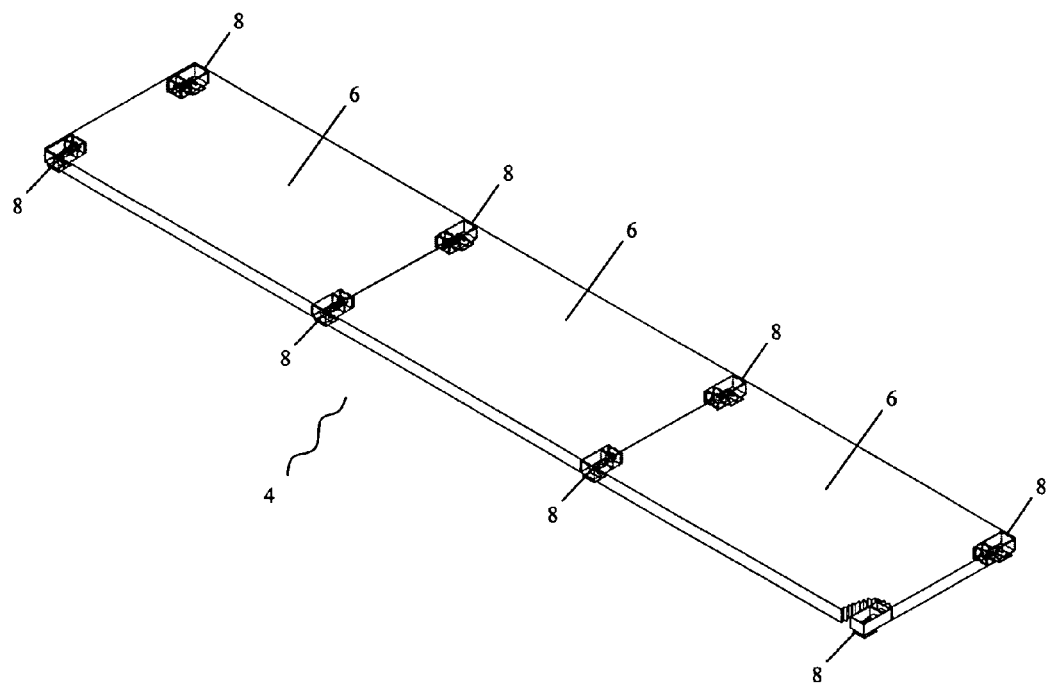
FIG. 1 is a perspective view of a scale including multiple load cells.

FIG. 1 is a perspective view of a scale 4 that utilizes a load-bearing platform 6 and one or more mounted load cells 8 positioned near certain points along the load-bearing platform 6. The load-bearing platform 6 is supported by the active ends of the load cells 8 so that when a load is placed on the scale 4, a force is applied in the direction of sensitivity of the load cells 8. The direction of sensitivity for the load-bearing devices 8 is usually the direction of gravitational force. The output of the load-bearing devices 8 are adjusted so that the magnitude of the collimated force or total force that is applied in the direction of sensitivity of the force sensors in the load cells 8 is unaffected by the presence of multiple load-bearing devices. The total force, or the weight of the load, on the scale is the sum of the force measurement of each of the load cells 8, as is well known. The force that is sensed is hardly affected by deflection in the load-bearing platform 6. Although the scale 4 may be a general purpose scale used to weigh anything from a person to a truck, it is especially well suited for applications where deflections or misalignments are expected. For example, the scale 4 may be used as a truck scale that deflects to divert the energy of stopping and starting from the load cells and reduces misalignment caused by the differential thermal expansion between the scale and its foundation.

Figure 2A:
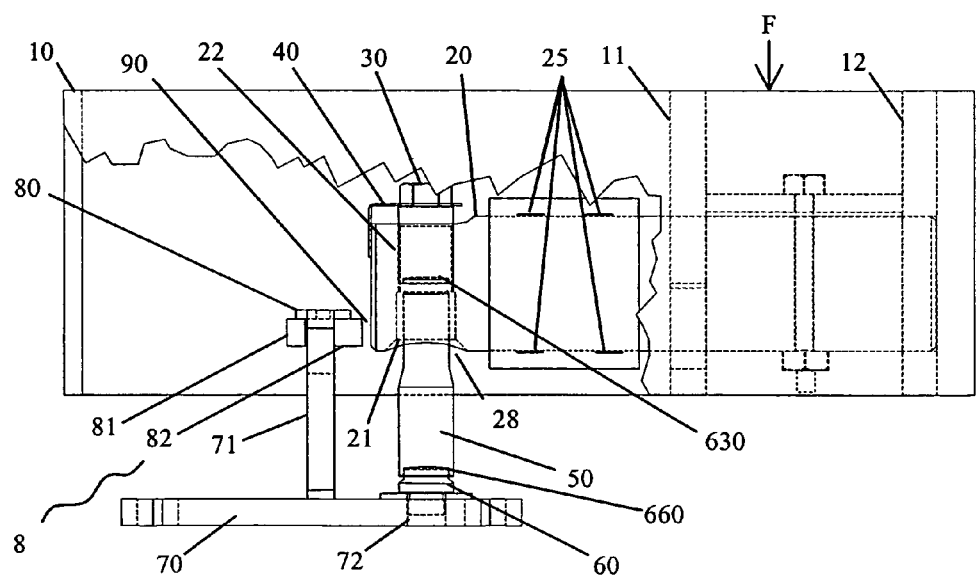
FIG. 2A is a side view of a first embodiment of a load cell in accordance with the invention, wherein the load cell is mounted within a scale.

FIG. 2A is a side view of one embodiment of the load cell 8 in accordance with the invention. The mounted load cell 8 is shown partially enclosed within a scale structure 10. The mounted load cell 8 includes a force-sensing unit 20 that is supported by a support structure 50, which is coupled to a base 70. When a load is placed on the load-bearing platform 6 (see FIG. 1), the weight of the load causes a vertical deflection of the force-sensing unit 20, which leads to detection of the applied force. The force-sensing unit 20 includes strain sensors 25 (see FIG. 5D) that are affected by the relative deformation of the force-sensing unit 20.

In FIG. 2A, the force-sensing unit 20 is attached to the scale structure 10 with contacting members 11 and 12. The contacting members 11 and 12 transfer the supported force to the base 70 through the force-sensing unit 20 and the support structure 50. The force sensing coupling unit 30 is connected to the force-sensing unit 20 with a threaded hole 22 and a clearance hole 21, which extend vertically through an opening 28 in the scale structure 10. The force sensing coupling unit 30 transfers the force on the support structure 50 to the load sensing unit 20 through a first interface 630. The threaded hole 22 provides a means for vertical adjustment to allow loads to be more evenly supported by the multiple force sensing units in the scale 4. A locking device 40 prevents the vertical adjustment of the force sensing coupling unit 30 from happening accidentally, without deliberate adjustment. The support structure 50 is supported through its second interface 660 by a base-coupling element 60 that is supported on the base 70 in a locating hole 72. The base 70 is attached to and is supported by a foundation as is well known and has a checking plate 71 attached vertically to it to provide a reference for both longitudinal and lateral movement limiting means. The base 70 is located on the foundation so that longitudinal clearance between the checking plate and the scale structure 10 limits the scale movement in its direction of length. A lateral stop 80 is supported by the checking plate 71 with a narrow side 81 and a wide side 82, which provide a coarse adjustment of lateral clearance 90 between the lateral stop 80 and the load sensing unit 20, limiting the scale movement in the direction of an arrow 87.

As used herein, the force coupling mechanism included in the force-sensing unit 20 is referred to as "a first force coupling mechanism" and the force sensor connected to the base 70 is referred to as "a second force coupling mechanism."

Figure 2B:
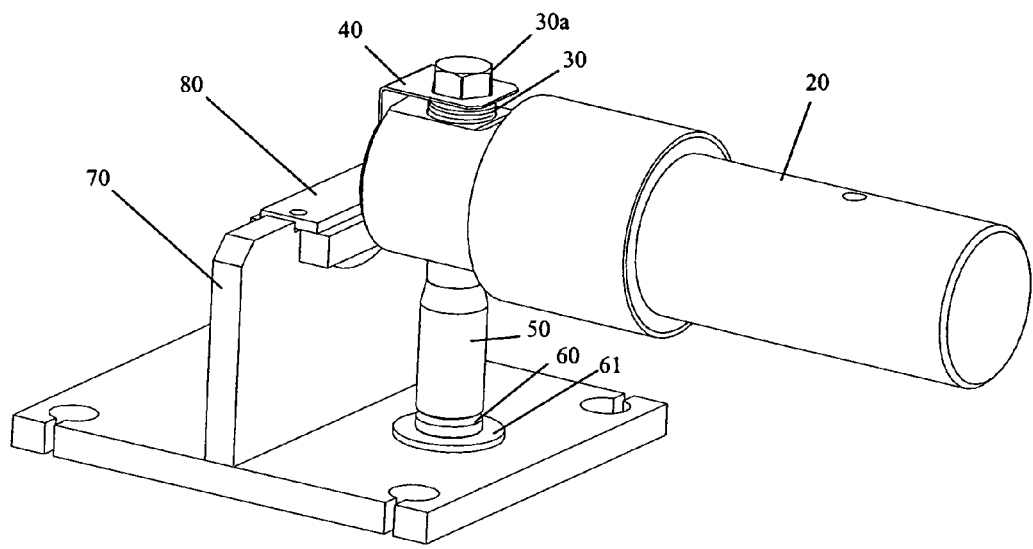
FIG. 2B is a perspective view of the load cell in FIG. 2A without the scale.

FIG. 2B is a perspective view of the load cell 8 of FIG. 2A without the scale structure 10. The lower end of the support structure 50 is supported on the base 70 by a base-coupling element 60. The base-coupling element 60 is supported on the base 70 by extending into the hole 72. A hardened support 61, such as a washer, may be inserted between the base 70 and the base-coupling element 60 to reduce the contact pressure if the base 70 is made from low strength metal. In the embodiment of FIGS. 2A and 2B, the force-sensing unit 20 has an opening 28 that extends through a thickness of the force-sensing unit 20. The support structure 50 is coupled to a force-sensor coupling element 30 to form a combined structure that extends through the opening 28. In this particular embodiment, the force-sensor coupling element 30 has a head 30a to facilitate turning it in the threaded hole 22 to adjust vertical positioning. The locking device prevents the force-sensor coupling element 30 from turning after adjustment. The direction of sensitivity of the load cell 8 in FIGS. 2A and 2B are shown by arrows labeled "F."

Figure 3:
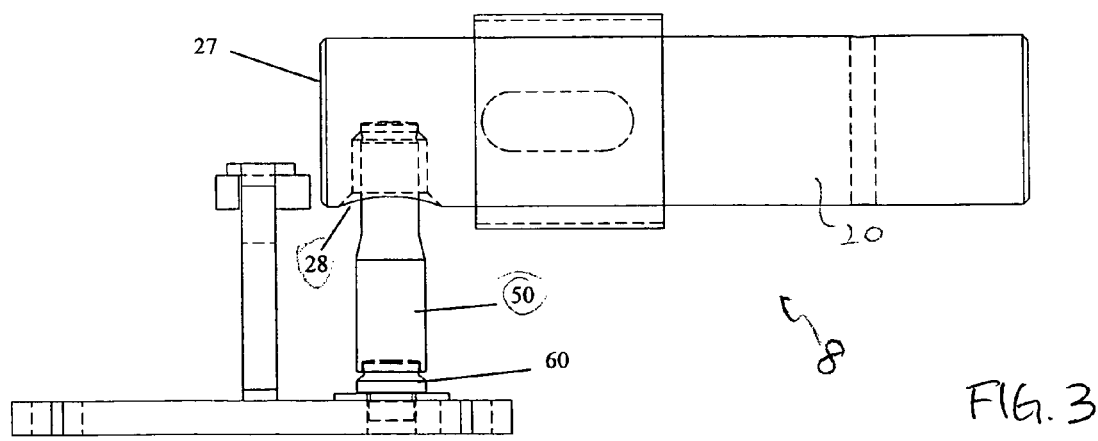
FIG. 3 is a side view of a second embodiment of a load cell in accordance with the invention.

FIG. 3 is a side view of an alternative embodiment of the load cell 8 in accordance with the invention, without the scale structure 10. This embodiment is similar to the embodiment shown in FIG. 2A and FIG. 2B, with the main difference being that the opening 28 does not extend all the way through the thickness of the force-sensing unit 20. Instead, the support structure 50 extends into the opening 28 that extends part-way into the force-sensing unit 20. The inside of the opening 28 is shaped so that the upper portion of the support structure 50 supports the load on the force-sensing unit 20 with the first interface 630 as used in the embodiment of FIGS. 2A and 2B. This embodiment of FIG. 3 does not include the optional vertical positioning threads 22, the force sensing coupling element 30, or the locking device feature 40 (see FIGS. 2A and 2B). The support structure 50 is coupled to the base 70 in substantially the same manner as the embodiment of FIGS. 2A and 2B.

Figure 4A:
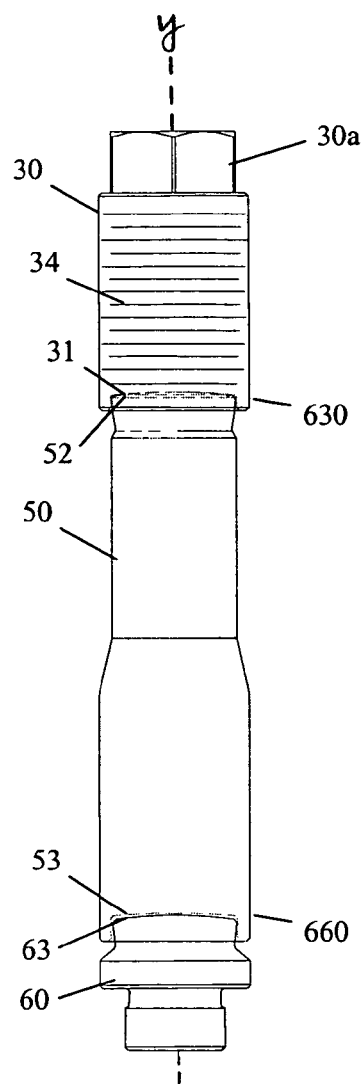
FIG. 4A is a side view of a support structure in accordance with the invention, in an undeflected state.

FIG. 4A is a side view of an embodiment of the support structure 50 in accordance with the invention, in an undeflected state. The support structure 50 is located between a force-sensor coupling element 30 and a base-coupling element 60. In its undeflected state, the support structure 50 is concentrically arranged with the force-sensor coupling element 30 and the base-coupling element 60. In particular, a vertical axis y extends through the center of all three elements when they are concentrically arranged in an undeflected state. The force-sensor coupling element 30 interfaces the support structure 50 at a first interface 630. Likewise, the base-coupling element 60 meets the support structure 50 at a second interface 660. The first interface 630 and the second interface 660 are each made of a convex surface and a concave surface of different dimensions, in accordance with the invention. For example, in the embodiment shown, the first interface 630 is made of a convex surface 52 of the support structure 50 contacting a concave surface 31 in the force-sensor coupling element 30. The second interface 660 is made of a convex surface 63 of the base-coupling element 60 contacting a concave surface 53 of the support structure 50. Preferably, the convex surfaces and the concave surfaces described herein are oblate spheroid surfaces. In the embodiment shown, the concave surfaces 31 and 53 have larger diameters than the convex surfaces 52 and 63, allowing the contacting areas to shift positions as the support structure 50 is tilted, establishing a rolling action.

In the particular embodiment that is shown, the force-sensor coupling element 30 includes threads 34 on the outer surface that accommodate a head 30a. The force-sensor coupling element 30 may be fixed to the force-sensing unit 20 (see FIG. 2A) by using the head 30a and the locking device 40 (see FIG. 2A). The threads 34 constitute a part of a vertical positioning feature that allows the load to be uniformly applied to the support structure 50.

Figure 4B:
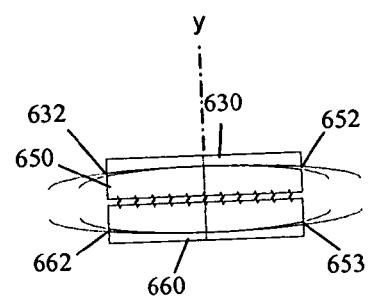
FIG. 4B is a cross-sectional view of the interfaces in a support structure in accordance with the invention, in an undeflected state.

FIG. 4B is a cross sectional view of the shapes of the first interface 630 and the second interface 660 without showing the entire height of the support structure 50. The interface between the convex and the concave oblate spheroid surfaces are illustrated more clearly than in FIG. 4A. In the undeflected state under load, the contact areas at the first and second interfaces 630, 660 form near the center (close to the axis y). Away from the center and near the edge, the convex surfaces do not contact the concave surfaces, thereby creating gaps 632 and 652 near the edges of the first interface 630, and creating gaps 662 and 653 near the edges of the second interface 660. The size of the contact area and the gaps depend on the load and the radius of curvature of the oblate spheroid surfaces at the interfaces 630 and 660.

Figure 4C:
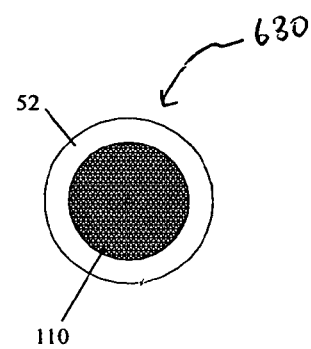
FIG. 4C is an illustration of an interface of the support structure at an interface, in an undeflected state.

FIG. 4C is an illustration of the convex surface 52 at the first interface 630 in FIG. 4A and FIG. 4B. A contact surface 110 is located near the center of the circular interface 630 as shown. The area of the convex surface 52 that is near the edge does not contact the concave surface 31 because of the gaps 632, 652, 662, and 653 (see FIG. 4B). The contact surface 110 has a substantially round shape when the support structure is cylindrical in shape, as shown, and in an undeflected state.

Figure 5A:
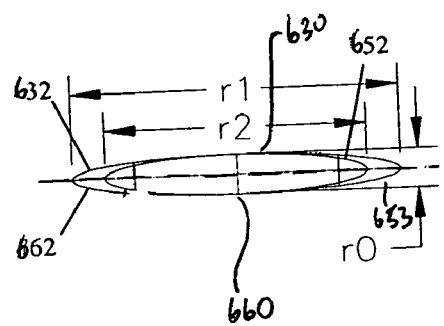
FIG. 5A is a geometric illustration of the interfaces in the support structure in FIG. 4B.

FIG. 5A is a geometric illustration of the ellipses that are rotated to form the interface surfaces in the support structure 50. As shown, juxtaposition of the cross-sections of the first and the second interfaces 630, 660 results in the parts of two concentric ellipses. The concave surface 31 is shown as an outside ellipse having a first major axis r1 and the convex surface 52 is shown as an inside ellipse having a second major axis r2, which is different from r1. The outside and inside ellipses have a common minor axis r0. The difference between r2 and r1 results in formation of the gaps 632 and 652 at the first interface and the gaps 662 and 653 at the second interface 660. These gaps allow the contact areas of surfaces 52 and 63 to roll and move off-center when a horizontal force is applied to the force-sensing unit 20. "Major axis" is herein also referred to as "diameter."

As a result of having different major axes, the concave surface 31 and the convex surface 52 have different radii of curvature. The radii of curvature function preferably meet certain conditions. For example, the curvatures of the adjacent surfaces at the interfaces 630, 660 make the centers align when the support structure 50 is not deflected, and allow the smaller major axis to roll easily on the larger major axis, thereby isolating the supported structures from horizontal forces. Also, the radii of curvature allows the surface with the smaller major axis to roll relatively easily while maintaining contact with the surface with the larger major axis. Compared to conventional devices that use flat and large-radius interfaces, the oblate spheroid surfaces at the interfaces result in significantly less wear and tear on the support structure. The contact area, when undeflected, has a relatively large radius of curvature with a concentric pattern. When deflected, the contact area has a less uniform radius of curvature that results from the combined effects of the concentric and circumferential distribution of the load. The support structure 50 is designed to "deflect" or "tip" in response to horizontal force, and this tipping is accompanied by the contact area of surfaces 52 and 63 shifting off-center while maintaining contact with the surfaces 31 and 53, respectively, in a rolling action. The amount of horizontal force that is transferred by the support structure 50 correlates with a tip angle θ (see FIG. 6B below), which is a measure of how much the support structure 50 is tipped, and the height "h" of the support structure. The lower interface 660 is designed based on the same principles as the upper interface 630.

The changing curvatures of the convex and concave surfaces at the interfaces 630, 660 allow for the damping of the rocking motion in the force-sensors that frequently occur, e.g. from acceleration or deceleration of a load. The rolling of the convex surfaces that allows the support structure 50 to tip reduces inaccuracies caused by force components that act in a direction other than the direction of force sensor sensitivity. A load cell that uses the support structure 50 is able to resist the generation of the small forces from misalignment of the applied force to the direction of sensitivity on the force sensors or from the deflection of bridging elements between the force sensors.

Figure 5B:
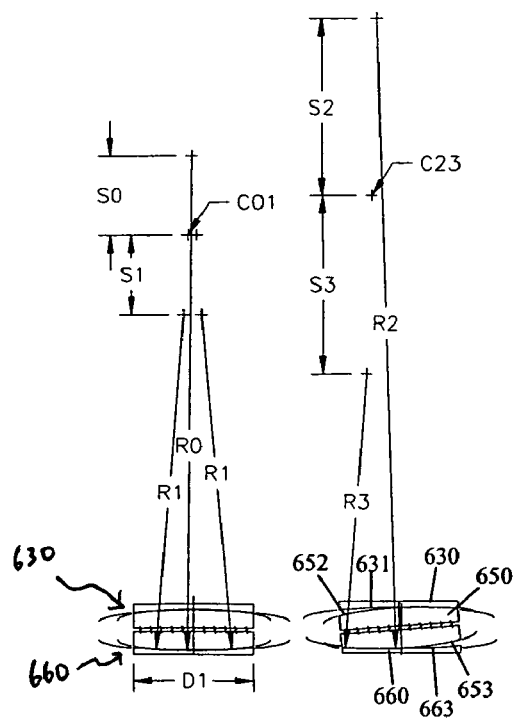
FIG. 5B is a cross-sectional view of the interfaces of the support structure in FIG. 4B and FIG. 6B illustrating the relative pivot points in the undeflected and deflected states.

FIG. 5B is a cross sectional view of the shapes of the first interface 630 and the second interface 660 without showing the entire height of the support structure 650. The relative radii of curvature are shown of the interface 660 in the center R0 and at the edges of the contact area R1 and R2. Without deflection under load, the contact areas at the first and second interfaces 630, 660 form near the center. Away from the center and near the edges of the interfaces, the convex surfaces do not contact the concave surfaces, thereby forming gaps in the contact area near the edges of the first interfaces 660, 630. The size of the contact area and the gaps depend on the load and the radius of curvature of the oblate spheroid surfaces at the interfaces 630 and 660. Because the surfaces are oblate, the radius in the center is greater than the radii near the edges. When the structure 50 is tilted, it rotates as a solid and despite the differences in curvature the entire surface moves about a more average radius of curvature whose center is located at point C01 a distance S0 from the center of R0 and a distance S1 from the center of R1. The angle of tilt tends to be the same for both the center and the edges of the contact area. The surface attempts to move a distance because of the tilt angle θ. A "center," as used herein, is a point at the distal end of a line segment, which is orthogonal to a curved surface having a length equal to the radius of curvature.

The distance moved in the direction of tilting by rotating a point on the surface with a radius of curvature R0 through angle θ is $\Delta x0 = \theta \cdot R0$ at the center point and $\Delta x1 = \theta \cdot R1$ for the edge points with radii of curvature R1. Since R0 is different than R1 a difference in the movement at the surface tends to occur.

$$\Delta x1 - \Delta x0 = \theta \cdot (R1 - R0)$$

The relative difference in curvature radii at the interfaces 630, 660 is greater in the invention than in the currently existing mechanisms. This larger difference in radii of curvature causes additional force upon movement that tends to absorb energy by the surfaces straining against one another, creating heat that dissipates the energy absorbed by this additional force. This additional force is only present during movement of the contact areas under load and is dependent on deflection, since the differences in curvature increases with the tilt angle as shown in FIG. 5B. It can be seen that the relative differences S2 and S3 from the average rotation point C23 have increased during the deflection, thereby increasing the differences in movement tendencies. On the trailing edge of the contact area with a radius of curvature R2 the movement tendency is in excess of the rotation about the average rotation point C23.

$$\delta xx2 = \delta \theta \cdot S2$$

On the leading edge of the contact area with a radius of curvature R3 the movement tendency is in deficient of the rotation about the average rotation point C23.

$$\delta xx3 = -\delta \theta \cdot S3$$

The result is two opposing-force regions in the support structure 50: one compressing at its leading contact area, and the other conversely stretching its trailing contact area. The base-coupling element 60 has a set of force regions opposing those in the support structure in its contact area. Near the edges of the contact area, the contact pressure is reduced as is well known. These forces on the surfaces are relieved as the areas move in a rolling action at the trailing edge, returning the materials to lower stress levels. No wear has been witnessed at the edges, and the theoretical reasons for this dramatic reduction in wear is beyond the scope of this disclosure. Without being bound to a specific theory, a possible explanation for this dramatic reduction in wear is that the stress fields produce thermo-elastic heating and cooling that generate expansion and contraction as well as heat loss without friction, causing energy absorption and dissipation.

Figure 5C:
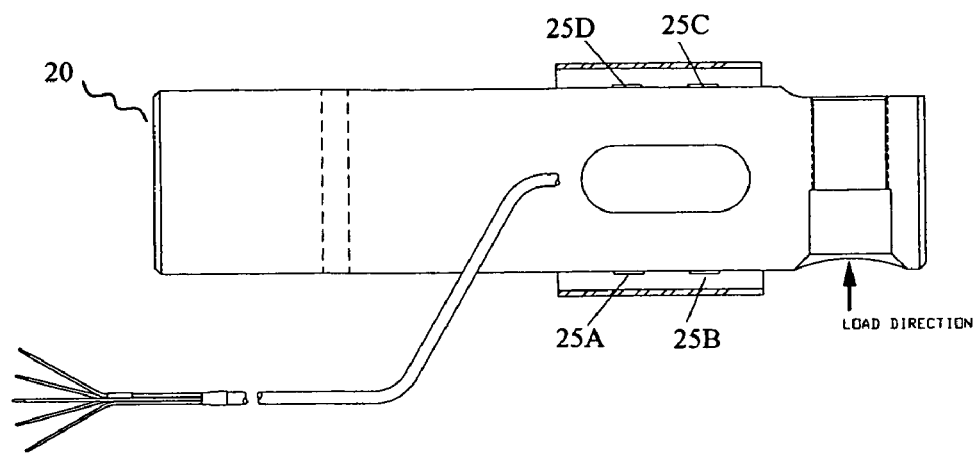
FIG. 5C is a partial view of the load cell in FIG. 2A.

FIG. 5C shows an exemplary embodiment of the force-sensing unit 20. Details about this particular force-sensing unit 20 are disclosed in U.S. Pat. No. 3,650,340 to Richard S. Bradley, which is incorporated by reference herein in its entirety.

Figure 5D:
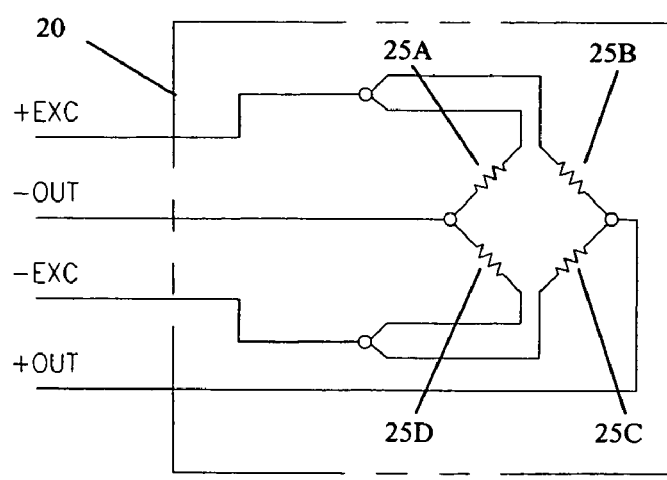
FIG. 5D is the electrical schematic of the strain sensors in the load cell in FIG. 5C and FIG. 2A.

FIG. 5D shows a well-known exemplary circuit including strain sensors 25A, 25B, 25C, and 25D in the force sensor 20 of FIG. 5C.

FIG. 6A is a cross-sectional view of the support structure 50 in accordance with the invention, in a deflected state. As mentioned above, the force-sensor coupling element 30 is fixed to the force-sensing unit 20 (see FIG. 2A), and therefore maintains a vertical alignment. Likewise, the base-coupling element 60 is fixed to the base 70 and maintains a vertical alignment. Therefore, when a horizontal force is applied, only the support structure 50 becomes deflected, as shown, by the convex surfaces 52 and 63 rolling at the interfaces 630, 660. When the support structure 50 tips, the force-sensor coupling element 30 and the base-coupling element 60 become misaligned and the axis y no longer runs through the center of the force-sensor coupling element 30 and the base-coupling element 60. For example, in FIG. 6A, while the axis y still runs through the center of the base-coupling element 60 but is off-center by a distance "d" from the force-sensor coupling element 30. This allows for the absorption of horizontal energy as an active load on the scale accelerates or decelerates.

FIG. 6B is an illustration of the interface 630 and the interface 660 when the support structure 50 is deflected. As the force-sensor coupling element 30 and the base-coupling element 60 remain in vertical positions while the support structure 50 tips, the contact area between the convex and the concave surfaces shifts off-center. At the interface 630, the contact surface moves to what is shown in the figure as the right side of the center. At the interface 660, the contact surface moves to what is shown in a direction opposite of the direction in which the shift occurs at the interface 630. As a result of the tipping of the support structure 50, the gaps 632 and 653 become larger. The amount of tipping may be measured by a tip angle θ. The larger the horizontal force (e.g., from vibration), the larger the tip angle θ. The centers of the two interfaces 630, 660 are misaligned by the distance "d." "h" represents the height of the support structure 50, only a part of which is shown in FIG. 6B.

FIG. 6C is an illustration of the shape of the interface 630 when the support structure 50 is tipped. When the support structure 50 tips, the shape of the contact surface 110 changes to a non-circular shape and shifts off-center. The axial misalignment of the force-sensor coupling element 30 and the base-coupling element 60 causes the strain to be only symmetric about the plane in which the parts axis lie during deflection. The changing curvature at the interface 630 shifts the contact area away from the central axis, redistributing the force in a direction perpendicular to this plane in both directions. A person of ordinary skill in the art will understand that FIG. 6C represents a state that is approximately a state of maximum deflection wherein the contact area is near the edge of the concave surface 31, and that a smaller force would cause a state of deflection between what is depicted in FIG. 4C and FIG. 6C. A person of ordinary skill in the art will also understand how to control the curvature of the convex surfaces 52 and 61 to achieve the desired goal. Normally, larger radii of curvatures in compressive load bearing surfaces cause lower contact stresses while smaller radii cause increased stress. The stress is not increased on this basis in the deflected invention due to this redistribution allowing smaller radii of curvature near the edges and increased tilting range "d" at shorter height "h."

One of the benefits of this invention is that it allows a design with a smaller effective height than a conventional design. The amount of contact area shifting that occurs at the interfaces 630, 660 upon deflection correlates with the amount of horizontal force that is transferred. Thus, in order to neutralize a horizontal force of a given magnitude, a certain amount of shifting of the contact areas occurs at the interfaces 630, 660. The convex and concave oblate spheroid contact surfaces of the invention allow greater contact area shifting at the interfaces 630, 660 in response to a given amount of force when it starts in the undeflected state, or the normal static state. The deflection being generated by an inertial force on the scale, the amount of shifting that results from a given force progressively decreases with the amount of shifting that is already done, at least partly due to a greater resistive force. With the shifting range, peak, restoring force, and energy absorption enhanced, the column 50 does not have to be as high as in a conventional (e.g., spherical) design to move the same amount horizontally and still have a low horizontal force when undeflected.

FIG. 7 is an illustration of the forces on the support structure 50 in FIG. 6A. FIG. 7 may be a snap shot of the support structure when a force is applied that has an element in the $F_0$ direction and an element in the $F_1$ direction. Alternatively, FIG. 8 depicts a snap shot of the support structure 50 tilted to its limit that is set by the scale structure 10. The scale structure 10 sets the tilt limit by closing a gap 91 and widening a gap 92. Impact with the scale structure 10 absorbs excess energy beyond what is absorbed by the invention through elastic flexing of more rigid metal structures. The $F_1$ element of the force causes the force-sensor coupling element 30 to shift in the direction of $F_1$, which in turn causes the support structure 50 to tip as shown. The tipping force $F_1$ has a reactive force $F_2$ in an opposite direction from $F_1$ on the force-measuring elements. The tipping reduces the horizontal force $F_1$ on the weight measurement, resulting in a more accurate measurement of the vertical force $F_0$. The energy absorbed (E) through deflection by a distance "d" (see FIG. 6B) is determined by the integration of the inertial force over the deflected distance "d," and is equal to the work done to stop the movement of the scale caused by the active force $F_1$:

$$E = \int_0^d F_1 \cdot dx.$$

For a peak force of $F_{1max}$ and a deflection of "d," the energy absorbed is approximately represented by an equation that assumes a linear function of force over distance:

$$E = \frac{1}{2} F_{1max} \cdot d.$$

The restoring force is equal and opposite to the active force, as is well known. The active force in the direction of $F_1$ is proportional to the vertical load $F_0$:

$$F_1 = \frac{F_0 \cdot R}{H}.$$

This indicates that in the absence of deflection, there is no side force. For small deflections, the side force is small. The resisting force is equal to the deflecting force. At maximum deflection, the scale stops moving and the resisting force becomes a restoring force that returns the scale to the static position once the motion is damped by the support.

FIG. 8 is an end view of the load cell 8 of FIG. 2A, wherein the support structure 50 is tipped. As shown, the tipping of the support structure 50 does not affect the overall dimensions or position of the load-sensing device 20, which provides space around the support structure 50 to accommodate the deflection in the opening 28 (see FIG. 2A).

FIGS. 9, 10, and 11 depict different embodiments of the support structure 50 in accordance with the invention. While the force-sensor coupling element 30 in the embodiment of FIG. 4A is a coupling mechanism that has a screw thread 34 to accommodate the threaded hole 22, the embodiment of FIGS. 9, 10, and 11 do not include threads 34 (see FIG. 4A). As shown, the shapes of the force-sensor coupling element 30, the support structure 50, and the base-coupling element 60 can be varied as deemed suitable by a person of ordinary skill in the art. Furthermore, the interfaces between different sections may also be changed.

FIG. 9 and FIG. 11 depict different embodiments of the concave surface 31 and the convex surface 52 that make up the first interface 630. In FIG. 9, the concave surface 31 is part of the force-sensor coupling mechanism 30 and the convex surface 52 is part of the support structure 50. In contrast, the positions of the concave surface 31 and the convex surface 52 are reversed in the embodiment of FIG. 11. In FIG. 11, the concave surface 31 is part of the support structure 50 and the convex surface 52 is part of the force-sensor coupling mechanism 30. Generally, the embodiment of FIG. 9 is preferable to the embodiment of FIG. 11 because the upward-facing concave surface 31 of FIG. 11 tends to collect dust and dirt unless a protective boot is provided. The embodiment of FIG. 11 is preferable to the embodiment of FIG. 9 with a boot because less machining is required and the coupling parts are the same.

FIG. 4A and FIG. 10 depict different embodiments of the concave surface 53 and the convex surface 63 that make up the second interface 660. In FIG. 4A, the convex surface 63 is part of the base-coupling element 60 and the support structure 50 has a concave surface 53 to accommodate the convex surface 63. In contrast, in FIG. 10, the convex surface 63 forms an end of the support structure 50 and there is a concave surface 53 on the base-coupling element 60. It is preferable to place the convex surface 63 on the base-coupling element 60 instead of on the support structure 50 where contamination is a concern because the concave surface 53, if positioned on the base-coupling element 60, faces upward and collects dirt and dust. The embodiments depicted in FIG. 9 and FIG. 10 have the least tendency for wear under extreme loads, since the total active and reactive forces are orthogonal to the contact surfaces and minimal surface shear is produced on the interface contact areas. The two types of surfaces in the positions of the concave and convex surface are herein also referred to as "an oblate spheroid surface" and "a counterpart oblate spheroid surface."

Figure 12:
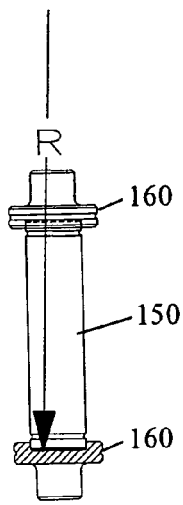
FIG. 12 depicts a side view of a conventional rocker pin that may be used in a load cell.
Figure 13:
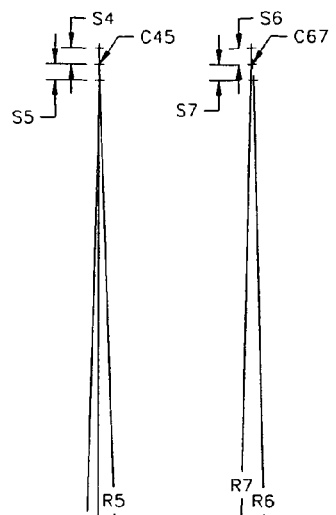
FIG. 13 is a cross-sectional view of the interfaces of the rocker pin in FIG. 12 illustrating the relative pivot points in the undeflected and deflected states.

FIG. 12 depicts a side view of a conventional rocker pin that may be used in a load cell. As shown, the rocker pin does not include interfaces of convex and concave surfaces to transfer horizontal and vibrational forces. FIG. 13 depicts an interface of a rocker column load cell as used by several scale manufacturers (e.g., Mettler Toledo, Fairbanks). This rocker column load cell also allows some tipping to transfer reduced horizontal forces. At interfaces 160, some tipping occurs, as shown. However, due to the absence of the concave and convex oblate spheroid surfaces, the amount of tipping that can occur is much more limited than in the support structure 50 of the invention. As a result, using the interfaces 160 require a greater height of the cylinder 150 that tips in response to horizontal forces. These rocker column load cells typically have fixed-end couplings with flat surfaces, and require large spherical-end radii on the support column 150 to prevent yielding on contact from heavy loads.

Figure 14A:
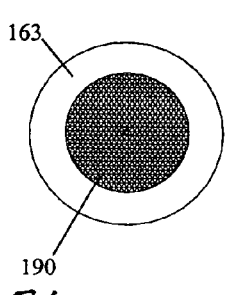
FIGS. 14A and 14B are illustrations of a contact surface in the rocker pin of FIG. 12.
Figure 14B:
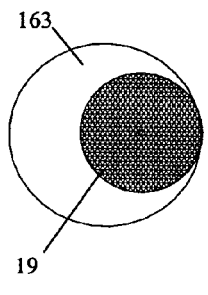

As shown in FIG. 14, a contact surface 190 at one of the interfaces 160 maintains the circular shape even when the contact area 190 is shifted in response to a horizontal force. The rocker column load cells have very little damping from the movement caused by inertial load on the scales. Thus, the time it takes for the scale to stabilize is of concern in many applications. The prior equations for the restoring force and the energy absorption are still valid. So, with greater height, the restoring force is reduced and less energy is now absorbed. Due to the use of spherical ends with uniform radii of curvature, the contact area does not change its shape. Some compression of the interface occurs, which produces a small variation of the curvature. Still, the enhanced effect on the shape of the contact area that is caused by the changing curvature of the invention is not realized by the rocker column load cells.

The applications for the invention include dynamic load applications where the structure supporting the load would be damaged without absorption of the dynamic energy such as in vibration inducing equipment or animal containers. High-resolution scale performance can be improved by the invention through the reduction of horizontal load cell forces and quick load response. Vehicle scales last longer and produce stable static weight measurements more quickly at lower cost using the invention.

The invention has been described using variations and examples to enable one skilled in the art to develop an understanding of the invention. Numerous variations will be obvious and as such, one skilled in the art should reference the claims of the invention rather than the foregoing examples to assess rights entitled to with respect to the claims.

What is claimed is:

1. A support mechanism for reducing an effect of horizontal force on load measurement, the support structure comprising a structure having surfaces with non-uniform radii of curvature at a first end and a second end, the first end and the second end forming interfaces with a force-sensor coupling element and a base-coupling element that are releasably engaged to the structure, wherein each of the interfaces includes a contact surface between a convex surface and a concave surface, wherein the concave surface has a larger major axis than the convex surface so that the contact surface is able to shift its position while maintaining contact with the concave and convex surfaces, reducing an effect of the horizontal force on vertical force measurements made by a force-sensing unit that is coupled to the support structure.

2. The support mechanism of claim 1, wherein the radii of curvature for the concave surface and the convex surface are such that a shape of a contact surface changes when the contact surface shifts position.

3. A support mechanism for reducing an effect of horizontal force on load measurement, the support structure comprising a structure having surfaces with non-uniform radii of curvature at a first end and a second end, the first end and the second end forming interfaces with a force-sensor coupling element and a base-coupling element that are releasably engaged to the structure, wherein each of the interfaces includes a contact surface between a convex surface and a concave surface, wherein the first end is a convex end and the second end is a concave end, the convex end forming a first contact surface with a concave surface of the force-sensor coupling element and the concave end forming a second contact surface with a convex surface of the base-coupling element.

4. A device for transferring collimated force while reducing diverse forces, the device comprising:
a structure;
a force-coupling mechanism coupled to the structure at a first interface, the first interface including a first contact area formed between a first convex oblate spheroid surface and a first concave oblate spheroid surface, wherein the first convex oblate spheroid surface and the first concave oblate spheroid surface have different radii of curvature; and
a base-coupling mechanism coupled to the structure at a second interface, the second interface including a second contact area formed between a second convex oblate spheroid surface and a second concave oblate spheroid surface, wherein the second convex oblate spheroid surface and the second concave oblate spheroid surface have different radii of curvature.

5. The device of claim 4 wherein a vertical axis runs through centers of the force-coupling mechanism, the structure, and the base-coupling mechanism in the absence of horizontal force, and wherein the structure tips in response to a horizontal force so that a deflected axis extending through a center of the structure forms an angle to the vertical axis.

6. The device of claim 5, wherein the tipping converts the horizontal force into a first horizontal force component applied at the first interface and a second horizontal force component applied at the second interface, wherein the first and the second horizontal forces act in opposite directions.

7. A load-measuring device having reduced sensitivity to the effect of a horizontal force in vertical force measurement, the device comprising a structure having a first oblate spheroid surface and a second oblate spheroid surface, the first oblate spheroid surface forming a first contact surface with a first counterpart oblate spheroid surface that is connected to a first coupling mechanism and the second oblate spheroid surface forming a second contact surface with a second counterpart oblate spheroid surface that is connected to a second coupling mechanism, wherein positions of the first and second contact surfaces shift positions when the structure tips in response to horizontal force.

8. The device of claim 7 further comprising a force sensing unit, wherein the first counterpart oblate spheroid surface is connected to the force sensing unit with the first coupling mechanism that extends through an opening in the force sensing unit, and wherein the first counterpart oblate spheroid surface allows vertical positioning of the structure relative to the first coupling mechanism.

9. The device of claim 7 wherein the first and second counterpart oblate spheroid surfaces have smaller diameters than the first and second oblate spheroid surfaces.

10. The device of claim 7, wherein the first and second counterpart oblate spheroid surfaces have different radii of curvature from the first and second oblate spheroid surfaces.

11. The device of claim 7, wherein the first oblate spheroid surface and the first counterpart oblate spheroid surface have a same minor axis but major axes of different lengths, the different major axes causing formation of a gap around the first contact surface.

12. The device of claim 7 further comprising a force sensing unit having an opening, wherein the structure is coupled to the force sensing unit by being inserted into the opening.

13. The device of claim 7, wherein the first and second contact surfaces have circular shapes in the absence of the horizontal force but change shapes in response to the horizontal force.

14. The device of claim 7, wherein the first oblate spheroid surface is convex and the first counterpart oblate spheroid surface is concave, so that the convex surface rolls within the concave surface.

15. The device of claim 7, wherein the tipping of the structure converts the horizontal force into a first horizontal force component applied at the first contact surface and a second horizontal force component applied at the second surface, wherein the first and the second horizontal forces have opposite directions, thereby providing a restoring moment that returns the support structure to its undeflected position, preventing the horizontal force from affecting vertical force measurement.

16. A load-measuring device having reduced sensitivity to the effect of a horizontal force in vertical force measurement, the device comprising:
a load sensing structure having a first oblate spheroid surface and a second oblate spheroid surface, the first oblate spheroid surface forming a first contact surface with a first counterpart oblate spheroid surface that is connected to a first force coupling mechanism and the second oblate spheroid surface forming a second contact surface with a second counterpart oblate spheroid surface that is connected to a second force coupling mechanism, wherein positions of the first and second contact surfaces shift positions when the structure tips in response to horizontal force.

* * * * *